(12) United States Patent
Nakamura et al.

(10) Patent No.: US 6,390,674 B1
(45) Date of Patent: May 21, 2002

(54) THERMAL ANALYSIS APPARATUS AND METHOD CAPABLE OF ACCURATELY MEASURING A TEMPERATURE OF A LARGE DIAMETER SAMPLE

(75) Inventors: Nobutaka Nakamura; Kanji Nagasawa, both of Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/482,807

(22) Filed: Jan. 13, 2000

(51) Int. Cl.⁷ .......................... G01N 25/00; G01K 5/00; G01K 17/00
(52) U.S. Cl. ............... 374/187; 374/10; 374/1
(58) Field of Search ............... 374/10, 11, 12, 374/14, 15, 1, 187, 188, 33, 39, 129, 134

(56) References Cited

U.S. PATENT DOCUMENTS

| | | | | |
|---|---|---|---|---|
| 3,981,175 A | * | 9/1976 | Hammond, III et al. | 73/15 R |
| 5,356,217 A | * | 10/1994 | Sheffield | 374/45 |
| 5,439,291 A | * | 8/1995 | Reading | 374/11 |
| 5,988,875 A | * | 11/1999 | Gershfeld et al. | 374/10 |
| 6,095,681 A | * | 8/2000 | Kunt et al. | 374/45 |
| 6,146,012 A | * | 11/2000 | Nakamura et al. | 374/10 |
| 6,170,984 B1 | * | 1/2001 | Schawe et al. | 374/10 |

* cited by examiner

*Primary Examiner*—Diego Gutierrez
*Assistant Examiner*—Gail Verbitsky
(74) *Attorney, Agent, or Firm*—Adams & Wilks

(57) ABSTRACT

Under a same heating condition as a sample to be measured, a physical property is measured for a reference substance whose temperature dependency of a physical property value is previously known. Reversely, a temperature profile of the reference substance is read so that the temperature profile is applied to a physical property measurement result for the sample. Thus, thermal analysis for the large diameter sample is made accurately without the necessity of arranging a temperature sensor in the vicinity of the sample.

18 Claims, 1 Drawing Sheet

THERMAL ANALYSIS APPARATUS AND METHOD CAPABLE OF ACCURATELY MEASURING A TEMPERATURE OF A LARGE DIAMETER SAMPLE

BACKGROUND OF THE INVENTION

The present invention relates to a thermal analysis apparatus and a thermal analysis method to reveal how a physical property of a material varies with temperature. Particularly, the invention relates to a novel improvement for suppressing uncertainty in temperature measurement which inevitably occurs upon measuring a large-sized sample.

Thermal analysis is an approach used to analyze a change in a physical or chemical property of a material as a function of temperature, and based on simultaneous measurements of material temperature and physical property. Various thermal analytic methods have so far been developed depending on the kind of physical property to be measured, typical ones of which, if rearranged in relation between technique and physical property, are as follows.

Differential scanning calorimetry (DSC): differential heat flow

Thermogravimetric measurement (TG): weight

Thermomechanical analysis (TMA): dimension

Dynamic thermomechanical analysis (DMA): modulus of elasticity

Dielectric thermal analysis (DETA): dielectric constant

In these thermal analysis methods, sample temperatures have been measured by temperature sensors such as thermocouples and resistor thermometers arranged in the vicinity of samples.

In order to accurately measure the temperature of a sample, it is desired to avoid a temperature distribution in the sample. Due to this, it is a general practice in thermal analysis to conduct measurement by decreasing the amount of a sample as much as possible so long as the sensitivity of physical property measurement does not become insufficient. The technique of reducing sample amount is effective for many applications where ingredient distribution in a sample does not cause problems. Particularly, significant effects are available in DSC and TG. Further, in DSC and TG, temperature distribution is suppressed by accommodating a sample in a vessel formed of aluminum or the like as a good heat conductive material. Furthermore, a temperature sensor such as a thermocouple contacted with a sample vessel is used for temperature detection.

That is, it is possible in DSC and TG to satisfy comparatively easily three elements of sample amount decrease, homogeneous sample heating by a good heat conductive vessel, and contact between a sample and a temperature sensor. As a result, they greatly contribute to accurate measurement of sample temperature.

However, in the case of TMA or DMA, it is difficult to satisfy, such conditions as sample amount decrease and homogeneous heating due to a vessel, of the three conditions to be easily satisfied by DSC and TG. Thus, situations become severe to accurately measure sample temperature.

DSC and TG in nature are not concerned with sample shape whereas in TMA information about sample length is important. For example, in expansion coefficient measurement as one of the important applications for TMA, it becomes requisite to know concretely a sample initial length. DMA deals with a modulus of elasticity as a ratio of stress to strain caused in a sample. Then, in order to accurately determine a modulus of elasticity, it is essential to accurately know at least a sample three dimensional shape.

That is, in TMA and DMA the sample tends to increase in diameter and hence a technique cannot be used to improve measurement accuracy of sample temperature, such as sample amount decrease and homogeneous heating.

Further, because of the restriction that no effect should be caused to reduce high accuracy dimensional measurement or strain measurement, it is difficult to put a temperature sensor in contact with a sample center. Moreover, even if measurement could be conducted with a temperature sensor contacted with a sample, a problem arises due to a temperature distribution caused by diameter increase such that it is uncertain whether a measured sample temperature correctly represents a sample overall temperature.

As stated above, in TMA and DMA the sample tends to increase in diameter. Due to this, there has arisen a problem that sample temperature measurement is inaccurate.

In particular, when precisely determining the coefficient of thermal expansion, the amount of sample expansion can be determined comparatively accurately. However, it has been a bottleneck to precisely measure a sample temperature.

SUMMARY OF THE INVENTION

The present invention has been developed in order to effectively solve the above problems. In a thermal analytic technique such as TMA or DMA in which an increase in diameter of a sample is inevitable, first a reference substance having a known temperature dependency of a physical property value and a sample to be measured are measured in physical property at the same time within the same furnace or under the same heating conditions. Next, in place of measuring a sample temperature using a temperature sensor such as a thermocouple arranged in the vicinity of the sample, a physical property change signal obtained by measuring a physical property value of the reference substance is converted into a temperature change signal. At this time, if the reference substance and the sample were separately measured in physical property change under the same heating conditions, the physical change of the reference substance with respect to an elapsing time from a measurement start is converted into a temperature change in the sample with respect to the elapsing time. Hereinafter, the analysis is proceeded similarly to usual thermal analysis.

In this process, the physical property change of the reference substance is used as a temperature sensor. Even in a large diameter sample, reduction in temperature measurement accuracy does not occur as a result of an arrangement or contactability of a temperature sensor.

DETAILED DESCRIPTION OF THE INVENTION

Figure 1:
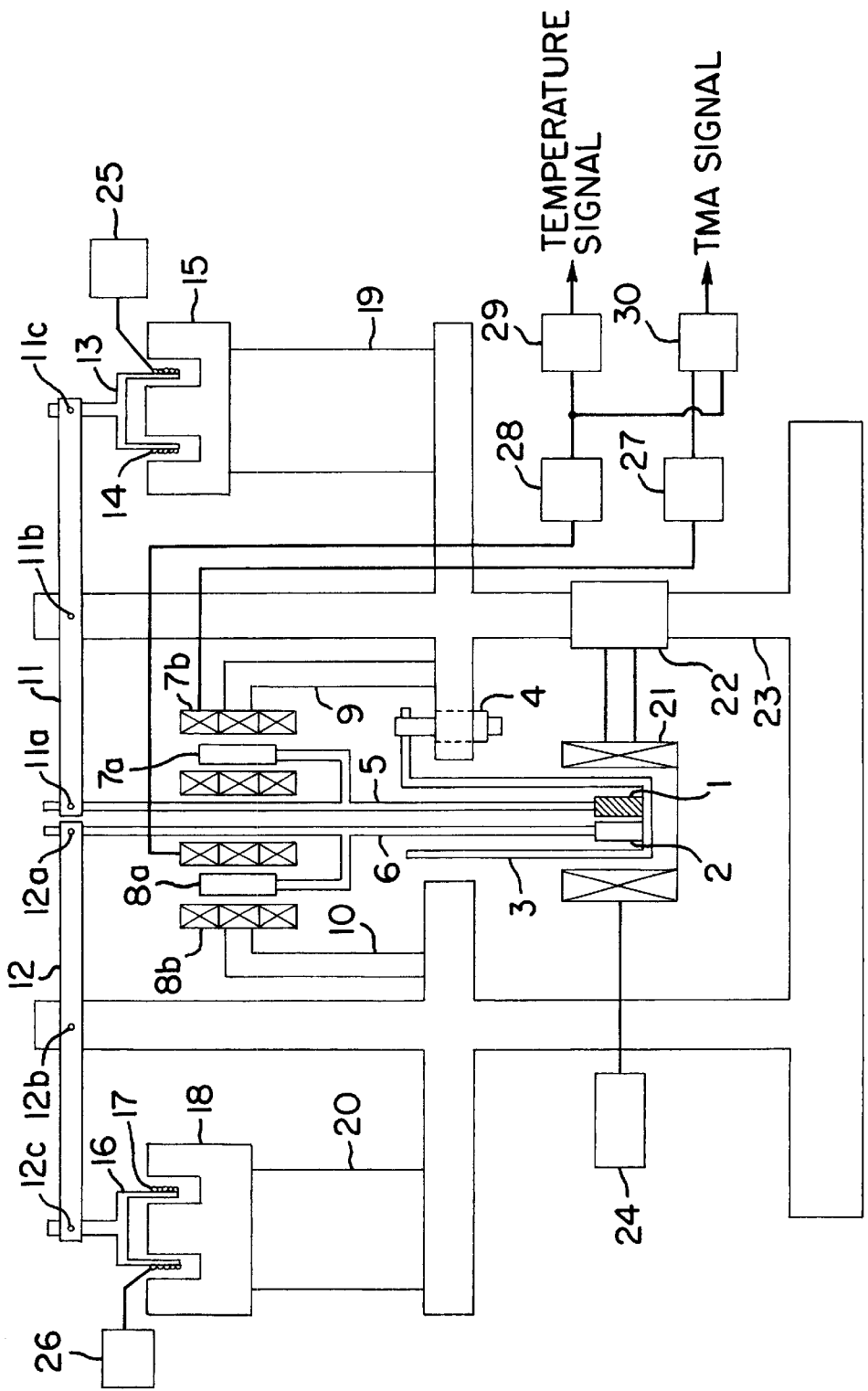
FIG. 1 is a sectional view partly having a block diagram showing one embodiment of the present invention.

Hereinafter, the present invention will be described in detail based on the drawings.

In FIG. 1, reference character 1 is a sample to be measured, and 2 is a reference substance having a known coefficient of thermal expansion. The sample 1 and the reference substance 2 are formed in a columnar shape. The sample 1 and the reference substance 2 are rested symmetrically on left and right sides on the bottom surface of a sample holder 3 formed in a bottomed tubular form of quartz glass as a low expansion material. On top surfaces of the sample 1 and reference substances 2, a sample side probe 5 and a reference side probe 6 are respectively rested which are made of quartz glass in a branched rod form.

The vertical displacements of the sample side probe 5 and the reference side probe 6 are detected as relative displacements by differential transformers 7b, 8b of cores 7a, 8a provided on a branch section, and measured by a sample expansion measuring circuit 27 and a reference expansion measuring circuit 28.

The sample holder 3 at its upper portion is fixed by a micrometer 4, for vertical movement relative to a housing 23. The differential transformers 7b, 8b are respectively fixed to the housing by holding members 9, 10.

The sample side probe 5 and the reference side probe 6 at top ends are respectively supported at probe fulcrums 11a, 12a of balance arms 11, 12 in rotatable manner.

The balance arm 11 has a main fulcrum 11b rotatably supported to the housing 23 and a coil fulcrum 11c supported with a coil holder 13. A coil 14 wound around a coil holder 13 is placed in a radial magnetic field created by a permanent magnet 15. The permanent magnet 15 is fixed to the housing 23 through a table 19.

Similarly, the balance arm 12 is rotatably supported at the main fulcrum 12b to the housing 23, while at the coil fulcrum 12c a coil holder 16 is supported. A coil 17 wound around the coil holder 16 is placed in a radial magnetic field created by a permanent magnet 18. The permanent magnet 18 is also fixed to the housing 23 through a table 20.

Load generating circuits 25, 26 respectively connected to the coils 14, 17 control current values flowing through the coils 14, 17 to control outputs of force generators formed by both the coil 14 and permanent magnet 15, and both the coil 17 and permanent magnet 18, respectively.

The differential transformer 7b is connected with the sample expansion measuring circuit 27 while the differential transformer 8b is connected with the reference expansion measuring circuit 28. The reference expansion measuring circuit 28 is connected with a reference expansion/temperature converter 29 to determine a temperature of a reference substance from an expansion amount of the reference substance. The sample expansion measuring circuit 27 and the reference expansion measuring circuit 28 are connected to a subtractor 30. The subtractor 30 determines a difference in expansion amount between the sample and the reference substance.

A furnace 21 is arranged around the sample holder 3. The furnace 21 can be vertically moved by a movement mechanism 22. The furnace 21 is controlled in temperature as a function of elapsing time from a measurement start time point by a temperature controller 24.

Hereinafter, the operation of an apparatus according to the present embodiment will be explained.

First, an operator operates the movement mechanism 22, and lowers the furnace 21 and sets a sample 1 and a reference substance 2 between the sample holder 3 and the sample-side probe 5 and reference-side probe 6. The operator sets loads to be applied to the sample 1 and reference substance 2 being measured to the load generating circuits 25, 26. As a result of this, a proper current flows through the coil 14, 17 due to operation of the load generating circuit 25, 26 so that vertical forces are delivered to the coil fulcrums 11c, 12c through the coil holders 13, 16. The forces applied to the coil fulcrums 11c, 12c are respectively conveyed to the probe fulcrums 11a, 12a through main fulcrums 11b, 12b of the balance arms 11, 12, and further applied to top ends of the sample 1 and reference substance 2 through the sample-side probe 5 and reference-side probe 6.

Then, the operator sets a desired temperature program to the movement mechanism 22, and runs a measurement, thereby changing the temperature of the sample 1 and reference substance 2 due to temperature scanning of the furnace 21. Before temperature scanning, when the entire apparatus is at a room temperature, the temperature of the furnace 21 is equal to a temperature of the sample 1 or reference substance 2. Accordingly, using the temperature of the furnace 21, it is possible to calibrate a temperature origin (room temperature) of the sample 1 and reference substance 2. However, if the temperature of the furnace 21 is scanned, generally a temperature difference of several degrees to several tens of degrees occurs between the furnace 21 and the sample 1 and the reference substance 2. Therefore, it is impossible to use the temperature of the furnace 21 as substitution for the temperature of the sample 1 or reference substance 2.

Although the sample 1 and reference substance 2 expand as the temperature rises, the amount of expansion at that time appears as relative displacement of core 7a, 8a to the differential transformer 7b, 8b provided at a branch portion of the sample-side probe 5 or reference-side probe 6, and each is detected by the sample expansion measuring circuit 27 or the reference substance expansion measuring circuit 28. Incidentally, strictly speaking, although the expansion amounts to be measured by the sample expansion measuring circuit 27 and reference expansion measuring circuit 28 are differences between the sample 1 and the sample holder 3, and between reference substance 2 and the sample holder 3, they can be neglected when the expansion amount of the sample holder is sufficiently small as compared with those of the sample 1 and reference substance 2.

Because the reference substance 2 has a known coefficient of thermal expansion, what the expansion amount is at a certain temperature is already known. In other words, it is possible to know the mean temperature of the reference substance 2 from an expansion amount of the reference substance 2. The reference expansion/temperature converter 29 acts to convert the expansion amount of the reference substance 2 into a temperature of the reference substance 2. Because the sample 1 and the reference substance 2 are in the same shape and placed symmetrical within the furnace 21, the temperature difference between the both is extremely small. The temperature of the reference substance 2 can be used as substitution for a temperature of the sample 1. Accordingly, the output of the reference expansion/temperature converter 29 represents a temperature signal for continuously measuring the sample 1 temperature.

In the case that the expansion of the sample holder 3 cannot be neglected, an accurate temperature can be determined if sending to the reference substance/temperature converter 29 the data extruding an affection of an expansion amount of the sample holder 3, i.e. the data of an expansion amount of the sample holder 3 added to an expansion amount measured by the reference expansion measuring circuit. In this case, the sample holder has a known coefficient of thermal expansion.

On the other hand, in the subtractor 30 is determined an output difference between the sample expansion measuring circuit 27 and the reference expansion measuring circuit 28, representing a differential expansion (difference in expansion amount) between the sample 1 and the reference substance 2. The effect of expansion of the sample holder 3 is cancelled and hence not contained in the output of the subtractor 30. Accordingly, the expansion amount of the sample 1 can be accurately determined by simply adding the known expansion amount of the reference substance 2 to the output of the subtractor 30. The resultant data are continuously outputted as TMA signal.

From a temperature signal and TMA signal of the sample 1 thus obtained, the analysis is further proceeded hereinunder similarly to the usual thermal analysis case.

Incidentally, the present embodiment was explained on the case that the physical property to be measured is a material expansion based on the structure of the differential type TMA apparatus. It is however natural that the application of the present invention is not limited to the differential type TMA apparatus. For example, if the reference substance and the sample are sequentially measured under a same condition, the present invention can be applied to a non-differential type TMA apparatus.

If the elastic modulus, dielectric constant or heat capacity of material is selected as a physical property to be measured, it is also possible to construct a DMA, DETA or DSC apparatus with high temperature measuring accuracy with the invention applied.

As discussed above, according to the present invention, because a temperature of a sample can be determined through observing an expansion amount of a reference substance, there is no necessity of arranging a temperature sensor such as a thermocouple in the vicinity of the sample. Accordingly, troublesome temperature calibration is unnecessary.

Further, because the reference substance entirety plays a role as a temperature sensor, there is no tendency of appearing a difference in heat capacity between the sample and the temperature sensor. Accordingly, temperature detection error will not appear that is due to a difference in thermal response between the sample and the sensor. For example, even where measurement efficiency improvement is emphasized and temperature scanning rate is raised, it is possible to suppress the reduction in temperature measurement accuracy to minimum.

Furthermore, because in principle a mean temperature including a temperature distribution inside the substance is outputted as a temperature signal, even where the sample is increased in diameter and a temperature distribution exists inside the sample, it is possible to accurately determine a sample mean temperature. That is, released from problems of temperature measurement resulting from relative position, contactability, contact point or the like of the large diameter sample and the temperature sensor, which occur in measurement by a conventional type temperature sensor.

As a result of this, for example, in a precise measurement of expansion coefficient wherein temperature measurement accuracy is important, measurement accuracy can be greatly improved. If in a measurement with same accuracy, it is possible to shorten a measurement time by increasing a temperature scanning rate as compared to the conventional method. Thus, measurement efficiency can be greatly improved.

What is claimed is:

1. A thermal analysis apparatus capable of accurately measuring the temperature of a sample while the sample is being heated without contacting the sample with a temperature detector, comprising: a reference having the same size and shape of the sample and having a known relationship between temperature and variations in a specific physical property thereof; a furnace for heating the sample and the reference over time, the sample and the reference being symmetrically disposed within the furnace; physical property measuring means for measuring changes in the physical property of the sample and the reference continuously over time; and a reference physical property value-temperature converter for converting a physical property measurement of the reference taken at each of a plurality of times into a temperature of the reference at the respective times so that the temperature of the reference represents the temperature of the sample so that thermal analysis of the sample may be conducted without using a temperature sensor in contact with or in the vicinity of the sample.

2. A thermal analysis apparatus according to claim 1; wherein the specific physical property is one of an expansion amount and an expansion coefficient of a material forming the reference and the sample.

3. A thermal analysis apparatus according to claim 1; wherein the furnace can heat the sample and the reference with high reproducibility with respect to an elapsing time after a start of measurement, and the reference physical property value-temperature converter for converting a measurement result of the physical property of the reference into a temperature of the reference uses as a parameter the elapsing time after measurement start.

4. A thermal analysis apparatus according to claim 1; wherein the reference has a known coefficient of thermal expansion.

5. A thermal analysis apparatus according to claim 1; wherein the sample and the reference are formed in a columnar shape.

6. A thermal analysis apparatus according to claim 1; further comprising a sample holder for holding the sample and the reference symmetrically within the furnace.

7. A thermal analysis apparatus according to claim 6; wherein the sample holder is formed of quartz and has a tubular form.

8. A thermal analysis apparatus according to claim 1; wherein the physical property measuring means comprises a vertical displacement measuring apparatus for measuring sample expansion, the vertical displacement measuring apparatus comprising vertically displaceable probes resting on surfaces of the sample and the reference, and differential transformers for measuring vertical displacement of the probes during thermal analysis of the sample.

9. A thermal analysis method capable of accurately measuring a temperature of a large diameter sample, comprising the steps of: providing a reference having the same size and shape as the sample, and having a known relationship between temperature and variations in a specific physical property thereof; determining a temperature of the sample at each of a plurality of times while the sample is being symmetrically arranged with respect to the reference in a furnace and heated by measuring variations in the physical property of the reference and converting the measured physical property of the reference into a corresponding temperature value based on the known relationship therebetween; and conducting thermal analysis of the physical property of the sample without placing a temperature detector in contact with or in the vicinity of the sample by measuring the reference and the sample within the same furnace or under the same heating conditions.

10. A thermal analysis apparatus capable of accurately measuring the temperature of a sample while the sample is being heated without contacting the sample with a temperature detector, comprising: a reference having the same shape as the sample and having a known relationship between temperature and variations in a specific physical property thereof; a furnace in which the reference and the sample are symmetrically disposed for heating the sample and the reference over time; physical property measuring means for measuring changes in the physical property of the sample and the reference continuously over time; and a converter for converting a physical property measurement of the reference taken at each of a plurality of times into a temperature of the reference at the respective times, the reference temperature being representative of the sample temperature so that thermal analysis of the sample may be conducted without placing a temperature detector in contact with the sample.

11. A thermal analysis apparatus according to claim 10; wherein the specific physical property is one of an expansion amount and an expansion coefficient of a material forming the reference and the sample.

12. A thermal analysis apparatus according to claim 10; wherein the furnace starts to heat the sample and the reference at a measurement start time, and physical property measurements are taken of the sample and the reference at the same points in time, so that the converter converts a measurement result of the physical property of the reference into a temperature representative of the sample temperature at the times when physical property measurements of the sample are taken.

13. A thermal analysis apparatus according to claim 10; wherein the reference has a known coefficient of thermal expansion.

14. A thermal analysis apparatus according to claim 10; wherein the sample and the reference have a columnar shape.

15. A thermal analysis apparatus according to claim 10; wherein the sample and the reference have the same shape and size.

16. A thermal analysis apparatus according to claim 10; further comprising a sample holder for holding the sample and the reference symmetrically within the furnace.

17. A thermal analysis apparatus according to claim 10; wherein the sample holder is formed of quartz and has a tubular form.

18. A thermal analysis apparatus according to claim 17; wherein the physical property measuring means comprises a vertical displacement measuring apparatus for measuring sample expansion, the vertical displacement measuring apparatus comprising vertically displaceable probes resting on surfaces of the sample and the reference, and differential transformers for measuring vertical displacement of the probes during thermal analysis of the sample.

* * * * *